United States Patent
Marx et al.

(10) Patent No.: US 10,525,259 B2
(45) Date of Patent: Jan. 7, 2020

(54) ATRAUMATIC VESTIBULAR STIMULATION AND MEASURING ELECTRODE

(71) Applicant: MED-EL Elektromedizinische Geraete GmbH, Innsbruck (AT)

(72) Inventors: Andreas Marx, Innsbruck (AT); Angelo De Marzo, Innsbruck (AT); Rami Saba, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 15/550,503

(22) PCT Filed: Mar. 3, 2016

(86) PCT No.: PCT/US2016/020543
§ 371 (c)(1),
(2) Date: Aug. 11, 2017

(87) PCT Pub. No.: WO2016/141112
PCT Pub. Date: Sep. 9, 2016

(65) Prior Publication Data
US 2018/0028803 A1 Feb. 1, 2018

Related U.S. Application Data

(60) Provisional application No. 62/128,556, filed on Mar. 5, 2015.

(51) Int. Cl.
*A61N 1/05* (2006.01)
*H04R 25/00* (2006.01)
(Continued)

(52) U.S. Cl.
CPC ....... *A61N 1/0541* (2013.01); *A61N 1/36036* (2017.08); *H04R 25/606* (2013.01);
(Continued)

(58) Field of Classification Search
CPC .............. A61N 1/0541; A61N 1/36036; A61N 1/36135; H04R 25/606; A61F 2/18; A61B 5/4023; A61B 5/04001
See application file for complete search history.

(56) References Cited

U.S. PATENT DOCUMENTS

2006/0271137 A1* 11/2006 Stanton-Hicks ..... A61N 1/0551
607/118
2011/0144733 A1 6/2011 Dadd et al.
(Continued)

FOREIGN PATENT DOCUMENTS

WO 2010135783 A1 12/2010
WO 2014179254 A1 11/2014

OTHER PUBLICATIONS

International Searching Authority, International Search Report—International Application No. PCT/US16/20543, dated May 19, 2016 together with the Written Opinion of the International Searching Authority, 8 pages.
(Continued)

*Primary Examiner* — Catherine M Voorhees
*Assistant Examiner* — Roland Dinga
(74) *Attorney, Agent, or Firm* — Sunstein Kann Murphy & Timbers LLP (57) ABSTRACT

A vestibular electrode is described that is for implantation into a vestibular semi-circular canal. An intra-labyrinthine electrode carrier with a C-shaped cross-section has an inner concave surface and an outer convex surface, and is configured to fit through an electrode opening in an outer surface of the bony labyrinth into the perilymph fluid without breaking the membranous labyrinth so as to fit the inner concave surface of the electrode carrier adjacent to the membranous labyrinth and the outer convex surface adjacent to the bony labyrinth. There are one or more electrode
(Continued)

contacts on a surface of the electrode carrier that are configured for electrical interaction with adjacent neural tissue.

11 Claims, 5 Drawing Sheets

(51) Int. Cl.
    *A61N 1/36*     (2006.01)
    *A61B 5/04*     (2006.01)
    *A61B 5/00*     (2006.01)
    *A61F 2/18*     (2006.01)

(52) U.S. Cl.
    CPC ......... *A61B 5/04001* (2013.01); *A61B 5/4023* (2013.01); *A61F 2/18* (2013.01); *A61N 1/36135* (2013.01)

(56) References Cited

U.S. PATENT DOCUMENTS

| | | |
|---|---|---|
| 2012/0078337 A1 | 3/2012 | Darley et al. |
| 2012/0095540 A1 | 4/2012 | Wahlstrand et al. |
| 2014/0228926 A1* | 8/2014 | Della Santina ...... A61N 1/0526 607/137 |
| 2015/0045864 A1 | 2/2015 | Howard |

OTHER PUBLICATIONS

Rubinstein, et al, "Implantation of Semicircular Canals with Preservation of Hearing and Rotational Sensitivity: a vestibular neurostimulator suitable for clinical research", NIH—Public Access Author Manuscript, Otology & Neurotology, 33(5), pp. 789-796, Jul. 2012.

* cited by examiner

ATRAUMATIC VESTIBULAR STIMULATION AND MEASURING ELECTRODE

This application is a national phase entry of Patent Cooperation Treaty Application PCT/US2016/020543, filed Mar. 6, 2016, which in turn claims priority from U.S. Provisional Patent Application 62/128,556, filed Mar. 5, 2015, which is incorporated herein by reference in its entirety.

TECHNICAL FIELD

The present invention relates to vestibular implant systems, and specifically a stimulation electrode for such systems.

BACKGROUND ART

Figure 1:
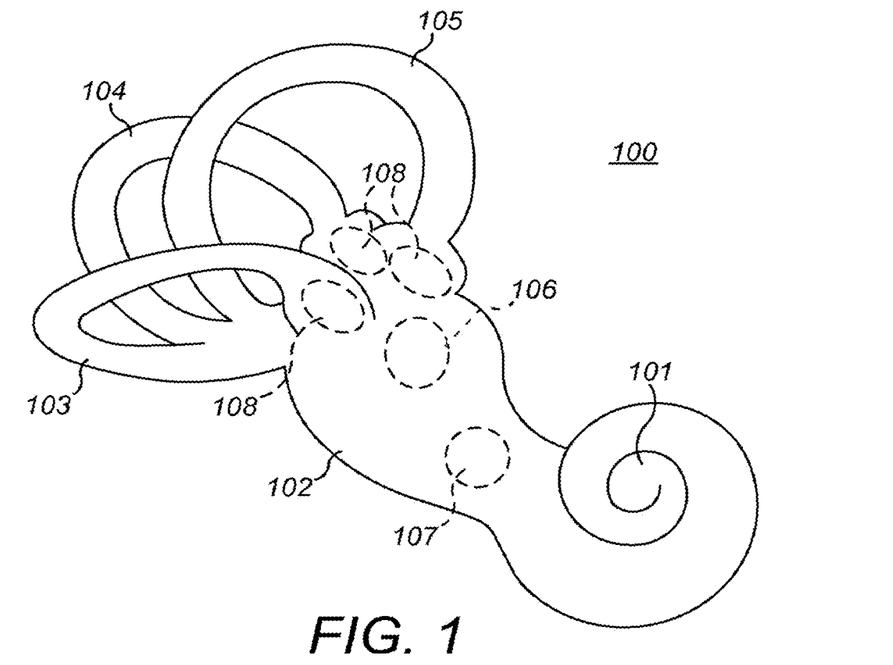
FIG. 1 shows the vestibular labyrinth of the inner ear.

The balance sensing and spatial orientation functionality of the brain is developed based on neural signals from the vestibular structures of the inner ear, one on each lateral side of the body. As shown in FIG. 1, each inner ear vestibular labyrinth 100 has five sensing organs: the ampullae 108 of the three semi-circular canals—the posterior canal 103, the superior canal 104, and the horizontal (lateral) canal 105—which sense rotational movement, and the utricle 106 and the saccule 107 in the vestibule 102, which sense linear movement.

Figure 2:
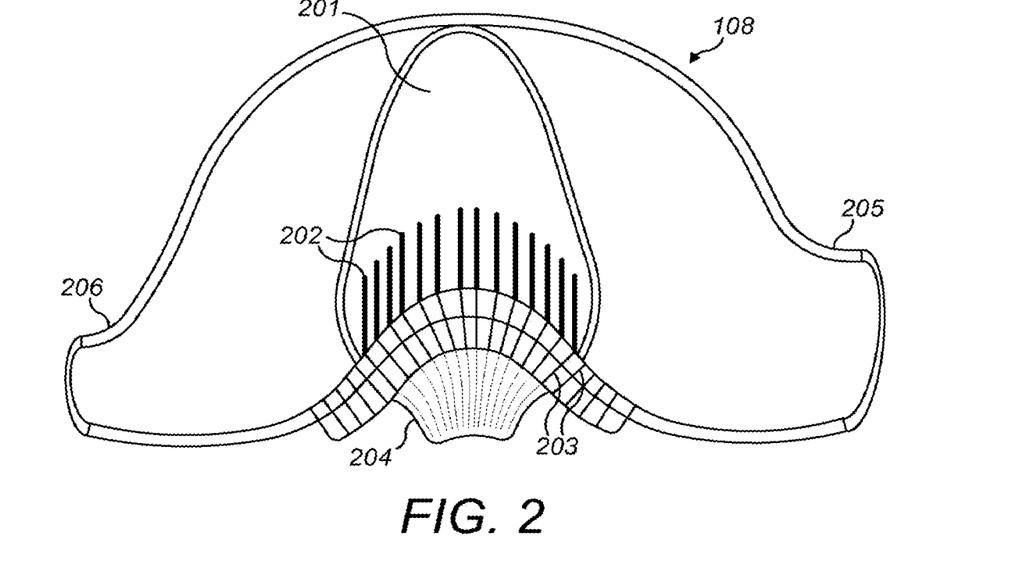
FIG. 2 shows anatomical detail of a vestibular canal ampulla.

FIG. 2 shows anatomical detail within a vestibular canal ampulla 108 which is connected at one end to the canal 206 and at the other end to the vestibule 205, and which contains endolymph fluid. The vestibular nerve endings 204 connect to the crista hair cells 203, the cilia ends 202 of which are embedded in the gelatinous cupula 201. When the head is stationary, the vestibular nerve endings 204 generate a baseline level of neural activity that is transmitted to the brain. When the head moves, the endolymph fluid within the respective ampulla 108 defects the cupula 201, that changes the neural activity level at the corresponding vestibular nerve endings 204 that correlates with the direction of head movement.

Unfortunately some people suffer from damaged or impaired vestibular systems in which the brain receives no inputs or meaningless inputs from the vestibular system. Such vestibular dysfunction can cause balance problems such as unsteadiness, vertigo and unsteady vision. Such sufferers lack the ability to balance and orientate, and instead have to rely on vision and proprioceptive inputs for balance.

The patient may also lose the vestibulo-ocular reflex (VOR), which allows for quick eye movements to compensate for head movement when focusing on a target. Without this VOR, the eyes cannot focus on the target during head movement (oscillopsia). With unilateral vestibular loss, the contralateral (non-diseased) inner ear is able to compensate and provide enough balance information. However, in the case of bilateral loss of vestibular function, the body can adapt to some extent by replacing the VOR reflex with the cervico-ocular reflex (COR), which sends signals from the neck to the eyes, saccades to keep the eyes focused on the target, or to implement strategies for eye movement based on anticipation or prediction. Despite this ability, in many patients vestibular function is not significantly restored and a vestibular prosthesis is needed.

Vestibular prosthesis systems are currently being researched that deliver electrical stimulation to the vestibular system to restore vestibular function to those who suffer from vestibular related pathologies. A vestibular prosthesis system needs to measure head movements and provide corresponding electrical stimulation patterns to the respective branches of the vestibular nerve. The prosthesis should be selective to avoid cross-talk and unintended stimulation of non-target vestibular nerve branches, and also to avoid stimulating other neighboring anatomical structures such as the facial nerve and the cochlear nerve. It is important for the prosthesis to have an atraumatic design that preserves hearing and any residual vestibular function, and so also preserves possibility of future alternative treatments. To preserve hearing, it is important to avoid penetration of the membranous labyrinth of the vestibular ampulla to preserve the volume of endolymph therein and maintain the natural ionic properties of the endolymph.

Experimental results indicate that electrical stimulation of the vestibular system has the potential to restore vestibular function, at least partially. See, e.g., Rubinstein J T et al., *Implantation of the Semicircular Canals With Preservation of Hearing and Rotational Sensitivity: A Vestibular Neurostimulator Suitable for Clinical Research*, Otology & Neurology 2012; 33:789-796 (hereinafter "Rubinstein"); Chiang B et al., *Design and Performance of a Multichannel Vestibular Prosthesis That Restores Semicircular Canal Sensation in Rhesus Monkey*, IEEE Trans. Neural Systems and Rehab Engineering 2011; 19 (5):588-98 (hereinafter "Della Santina"); and Gong W et al., *Vestibulo-Ocular Responses Evoked Via Bilateral Electrical Stimulation of the Lateral Semicircular Canals*, IEEE Transactions On Biomedical Engineering, Vol. 55, No. 11, November 2008 (hereinafter "Merfeld"); all incorporated herein by reference.

One challenge in developing a vestibular implant is the design of a device-to-body interface, the stimulation electrode. Such a vestibular stimulation electrode is inserted into the vestibular canal to selectively stimulate at least one of the vestibular nerve branches for the vestibular canal ampullae. Typically insertion of the stimulation electrode is though the semicircular canal. The stimulation electrode should be located as close as possible to the nerve fibers of the hair cells in the ampulla crista without damaging them.

Currently, different research groups are working on the development of different vestibular implants, with intra-labyrinthine stimulation approaches being of interest for the present purposes. U.S. Pat. No. 7,962,217 of the Merfeld group addresses Meniere's disease and is not intended for selective stimulation as required for treatment of vestibular disease. The Merfeld group also has published information on use different types of stimulation electrode including simple wires (Gong et al., *Vestibulo-Ocular Responses Evoked Via Bilateral Electrical Stimulation of the Lateral Semicircular Canals*, IEEE Transactions On Biomedical Engineering, Vol. 55, No. 11, November 2008), and polyimide thin film electrodes (Hoffman et al., *Design of Microelectrodes for a Vestibular Prosthesis*, BMT 2011 Rostock, Germany), though for the latter there is no published data.

The Rubinstein research group published details of a vestibular stimulation electrode in the previously cited Rubinstein article, as well as in U.S. Patent Publication 2012130465 and U.S. Patent Publication 2012/0226187. Their stimulation electrode has a relatively small diameter to prevent compression of the membranous canals using "soft surgery" techniques. They claim to have developed a vestibular stimulation electrode that allows post-surgical preservation of the natural function of the vestibular system.

The Della Santina research group published details of their stimulation electrode in the previously cited Chiang reference, as well as in U.S. Pat. No. 7,647,120 and PCT Patent Publication WO 2011088130. Their prosthesis is being developed for treatment of bilateral vestibular hypofunction (BVH) for which there is no absolute need to preserve natural vestibular function. The research and development strategy here accepts compression or other trauma to the membranous labyrinth in order to get the stimulation electrodes closer to the respective nerve branches. Since the membranous duct fills out almost the entire ampulla, it is virtually impossible to reach the crista without compressing or otherwise traumatizing the membranous canals.

All the above mentioned examples are electrodes that are intended to be inserted into the vestibular labyrinth, known as intra-labyrinthine electrodes. There are also extra-labyrinthine electrodes that are placed outside the vestibular labyrinth to stimulate the vestibular nerve. There are researchers that are attempting to locate such electrodes in close proximity to individual ampullary nerve branches of the vestibular nerve. The main advantages of using extra-labyrinthine electrodes is the preservation of the delicate intra-labyrinthine structures (which reduces the risk of generating a sensorineural hearing loss) and the closer distance to the addressed nerve branches.

The main disadvantages of extra-labyrinthine electrodes relate to the surgical accessibility of the ampullary nerve branches. When drilling in close proximity to nerves, there is increased risk of damaging the nerve. And to approach the lateral and superior ampullary nerve branches, parts of the ossicular chain need to be removed, which results in a conductive hearing loss. The lateral and superior ampullary nerve branches also are in close proximity to the facial nerve, which increases the risk of damaging the facial nerve and/or unintentionally stimulating it. So, even though extra-labyrinthine electrodes may preserve the intra-labyrinthine vestibular structures, they are traumatic for other anatomical structures and/or increase the risk of mechanically damaging the nerve during surgery.

SUMMARY

Embodiments of the present invention are directed to a vestibular stimulation electrode lead for implantation into a vestibular semi-circular canal. An intra-labyrinthine electrode carrier with a C-shaped cross-section has an inner concave surface and an outer convex surface, and is configured to fit through an electrode opening in an outer surface of the bony labyrinth into the perilymph fluid without breaking the membranous labyrinth so as to fit the inner concave surface of the electrode carrier adjacent to the membranous labyrinth and the outer convex surface adjacent to the bony labyrinth. There are one or more electrode contacts on a surface of the electrode carrier that are configured for electrical interaction with adjacent neural tissue.

An extra-labyrinthine electrode lead has a distal end connected to the electrode carrier at the electrode opening at a connection angle that is configured to avoid over-insertion of the electrode carrier. In such an embodiment, the electrode carrier may further have a carrier angle that is adapted to change the direction of the electrode carrier beyond the electrode opening so as to direct the electrode carrier between the bony labyrinth and the membranous labyrinth.

In specific embodiments, the electrode carrier may be configured so that after implantation into a vestibular semi-circular canal, the electrode carrier has a proximal end near the electrode opening and terminal distal end away from the electrode opening. The electrode carrier may be narrower at the distal end than at the proximal end, or the electrode carrier may be narrower at the proximal end and the distal end and wider in between.

The one or more electrode contacts may specifically be on the outer convex surface of the electrode carrier to face the bony labyrinth, or on the inner concave surface of the electrode carrier to face the membranous labyrinth, or both. And the one or more electrode contacts may include at least one stimulation contact for delivering an electrical stimulation signal to the adjacent neural tissue and/or at least one measurement contact for measuring electrical activity in the adjacent neural tissue.

Embodiments of the present invention also include a vestibular implant system having one or more electrode leads according to any of the foregoing.

BRIEF DESCRIPTION OF THE DRAWINGS

FIG. 3 A shows a longitudinal sectional view and FIG. 3 B shows a cross-sectional view of a vestibular electrode according to one embodiment of the present invention.

FIG. 4 A-B shows cross-sectional views of a vestibular electrode according to another embodiment of the present invention.

FIG. 5 A-B shows overhead views of a vestibular electrode carrier according to different embodiments of the present invention.

DETAILED DESCRIPTION

Embodiments of the present invention are directed to an atraumatic intra-labyrinthine vestibular electrode for selective electrical interaction with the vestibular nerve that avoids hearing impairment and damage to anatomical structures. The vestibular electrode provides for an insertion and placement that is as atraumatic as possible to preserve the delicate anatomical structures and residual functionality of the vestibular system and the inner ear, and thereby prevent or at least minimize any neurosensory loss.

Figure 3A:
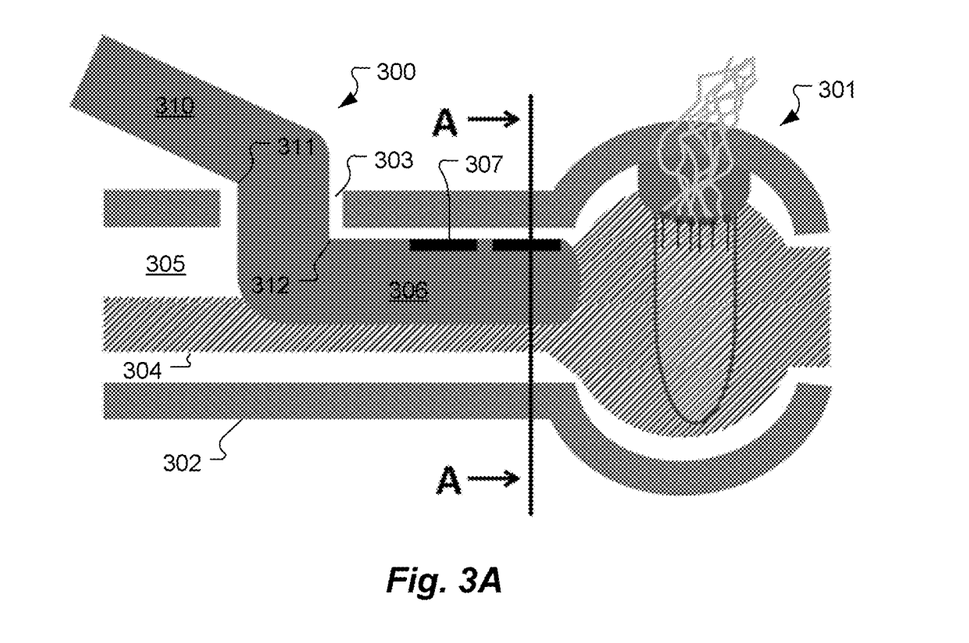
Figure 3B:
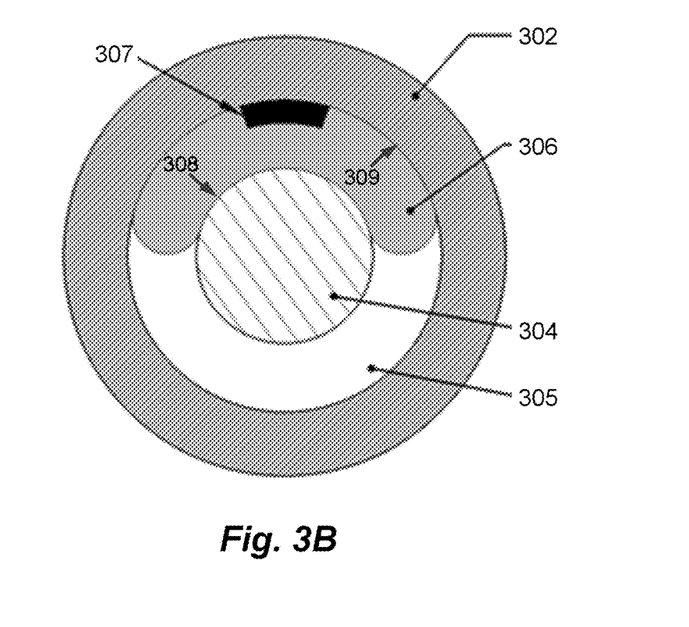

FIG. 3A shows a longitudinal sectional view and FIG. 3B shows a cross-sectional view of a vestibular electrode arrangement 300 for implantation into a vestibular semi-circular canal 301. By way of context, it is noted that the semi-circular canal 301 includes a bony labyrinth 302 having an internal volume that typically might have a radius of about 0.8 mm, which is filled with perilymph fluid 305 that surrounds a membrane labyrinth 304 that typically might have a radius of about 0.45 mm, and which contains endolymph fluid.

An intra-labyrinthine electrode carrier 306 has one or more electrode contacts 307 that are configured for electrical interaction with adjacent neural tissue. The electrode carrier 306 is configured to fit through an electrode opening 303 (also known as a labyrinthotomy) in the outer surface of the bony labyrinth 302 into the perilymph fluid 305. As can be seen in FIG. 3B, the cross-section of the electrode carrier 306 is C-shaped with an inner concave surface 308 and an outer convex surface 309, which are configured so that when the electrode carrier 306 has been fully inserted into position, the inner concave surface 308 lies adjacent to the membranous labyrinth 304 without breaking the membranous labyrinth 304 and the outer convex surface 309 lies adjacent to the bony labyrinth 302.

An extra-labyrinthine electrode lead 310 portion of the electrode arrangement 300 has a distal end connected to the electrode carrier 306 at the electrode opening 303 at a connection angle 311 that is configured to avoid over-insertion of the electrode carrier 306. The electrode carrier 306 also has a carrier angle 312 that is adapted to change the direction of the electrode carrier 306 beyond the electrode opening 303 so as to direct the electrode carrier 306 between the bony labyrinth 302 and the membranous labyrinth 304.

Figure 4A:
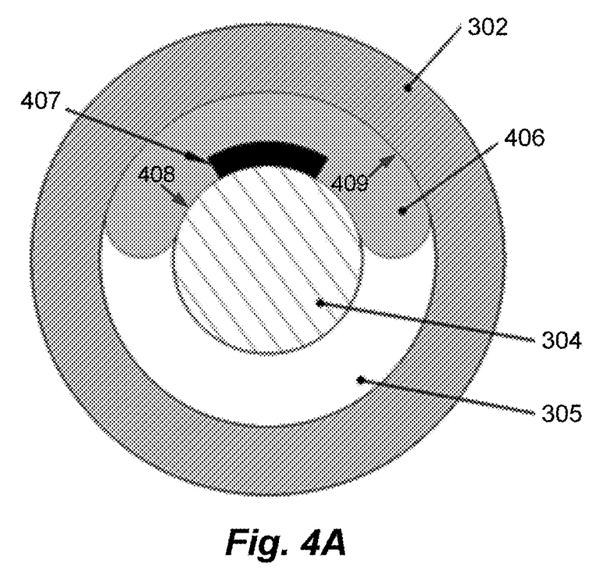

In the embodiment shown in FIG. 3B, the electrode contacts 307 specifically are on the outer concave surface 309 of the electrode carrier 306 to face the bony labyrinth 302. In another embodiment as shown in FIG. 4A, the electrode contacts 407 are on the inner convex surface 408 of the electrode carrier 406 to face the membranous labyrinth 304. In yet other embodiments, there may be one or more stimulation contacts 307/407 on each surface of the electrode carrier 306/406. And in any of these specific embodiments, the electrode contacts 307/407 might be about as wide as the radius of the membranous labyrinth 304, say 0.46 mm. And the electrode contacts 307/407 specifically may be stimulation contacts for delivering an electrical stimulation signal to the adjacent neural tissue and/or at least measurement contacts for measuring electrical activity in the adjacent neural tissue.

Figure 4B:
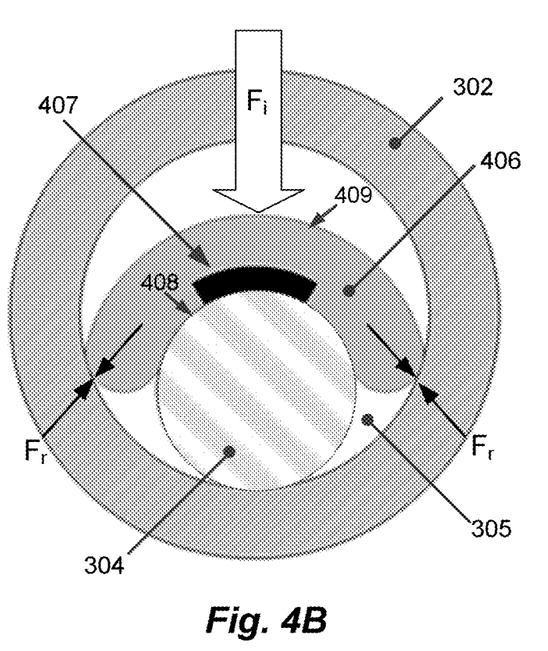

FIG. 4B shows how the downward insertion force $F_i$ as the electrode carrier 406 is inserted into the interior of the bony labyrinth 302 is widely distributed by the shape of the inner concave surface 408 over a large amount (about 46%) of the circumference of the membranous labyrinth 304 which is gently compressed by the insertion force $F_i$. During insertion, the radial outer ends of the electrode carrier 406 engage against the inner surface of the bony labyrinth 302 that generates a reaction force $F_r$ that eventually acts as an end stop to the insertion that also prevents overcompression of the membranous labyrinth 304 to preserve it intact without breaking. From that point on, no additional force will be introduced into the membranous labyrinth 304, and instead the stronger bony labyrinth 302 takes up the introduced insertion force. That means the electrode carrier 406 can be correctly positioned between the bony labyrinth 302 and the membranous labyrinth 304 regardless of the insertion angle of the electrode carrier 406, which naturally fits into the intended position. In a specific embodiment, the generally circular cross-section of the bony labyrinth 302, the C-shape of the electrode carrier 406 can be chosen such that the carrier attaches to the bony labyrinth 302 at an angle of 90° (+/−30°) when the radial outer ends of the electrode carrier 306 engage the bony labyrinth 302 as discussed above.

Figure 5A:
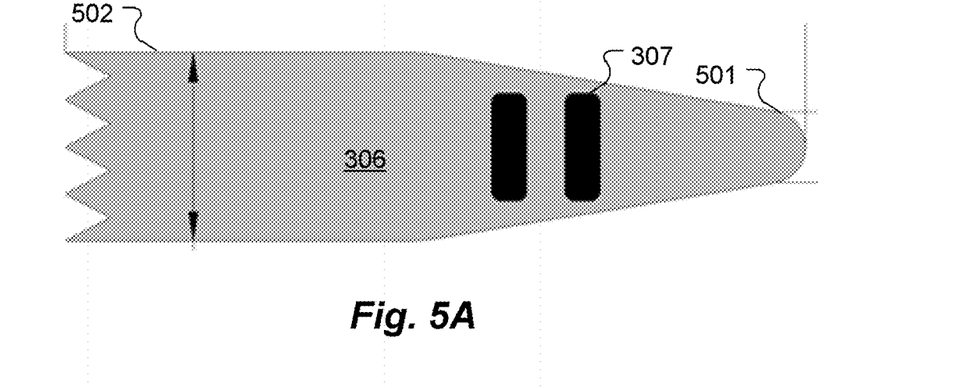
Figure 5B:
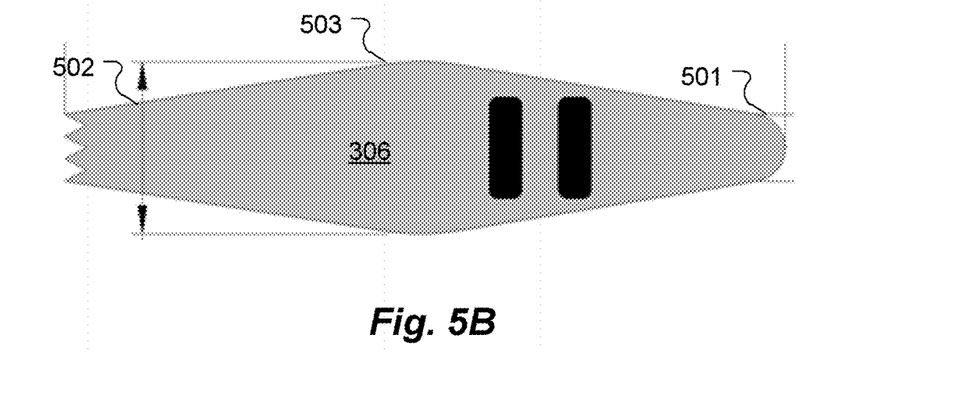

FIG. 5A-B shows overhead views vestibular electrode carriers according to different embodiments of the present invention with non-uniform widths. In FIG. 5A, the electrode carrier 306 has a length as shown of about 3 mm, with a proximal end 502 near the electrode opening that is about 0.88 mm in diameter. The electrode carrier 306 also has terminal distal end 501 away from the electrode opening that is narrower across than the proximal end 502; e.g., about 0.3 mm in diameter. This geometry may be advantageous during insertion of the electrode carrier 306. Alternatively as shown in FIG. 5B, the electrode carrier 306 may be narrower at the proximal end 502 and the distal end 501, and wider in between. This geometry may be advantageous during both insertion and explantation of the electrode carrier 306.

Figure 6:
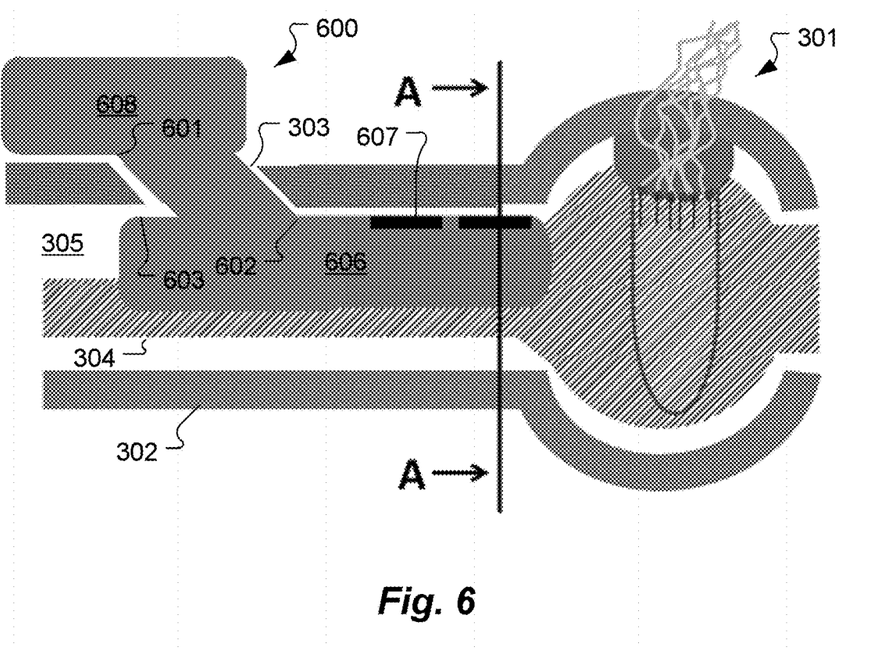
FIG. 6 shows a longitudinal sectional view of a vestibular electrode according to another embodiment of the present invention.

FIG. 6 shows a cross-sectional view of a vestibular electrode 600 according to another embodiment where the electrode carrier 606 is at a different angle where it passes through the electrode opening 303. That in turns means a different connection angle 601 at the distal end of the extra-labyrinthine electrode lead 308 so that it lies flat against the outer surface of the bony labyrinth 302. Similarly, there is a different carrier angle 602 within the bony labyrinth 302, as well as an anti-retraction heel 603 that projects from the proximal end of the electrode carrier 606 that resists post-surgical retraction of the electrode carrier 606.

Figure 7:
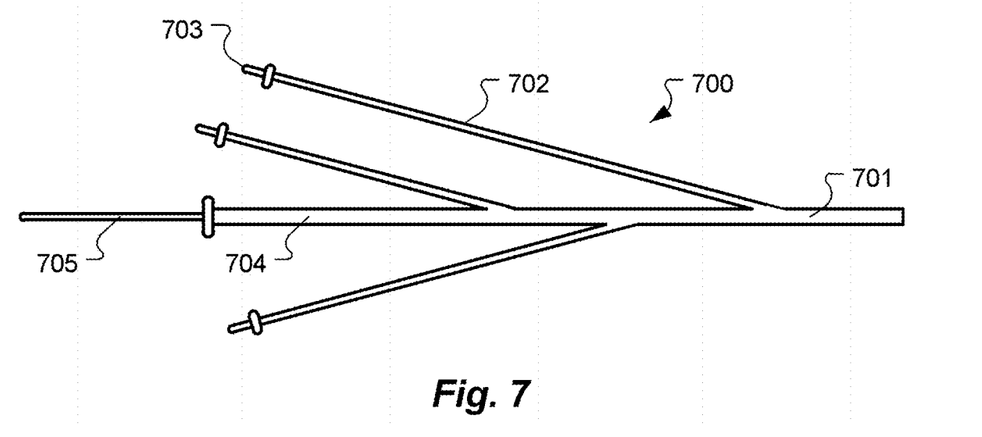
FIG. 7 shows an example of a combined electrode for a cochlear implant and a vestibular prosthesis.

FIG. 7 shows an example of a combined electrode 700 for a cochlear implant and a vestibular prosthesis. There are three vestibular electrode branches 702 with atraumatic electrode carriers 703, and the center branch is a cochlear implant electrode lead 704 and an electrode array 705 configured for insertion into the cochlea. The cochlear implant electrode array 705 also may have a C-shaped cross section to gain a similar benefit (i.e. reduced trauma) during cochlear insertion.

The C-shaped cross-section of the electrode carrier for such vestibular electrodes does not act as a piston during the insertion. This avoids increased hydrostatic pressure of the endolymph and perilymph and so causes less mechanical damage to the delicate anatomical structures. In addition, the inserted electrode carrier does not entirely fill the available space in the ampulla/semi-circular canal and allows the regular flow of the endolymph and perilymph.

The electrode carrier also has a larger surface of contact with the membrane as compared to prior art designs, which generates less mechanical pressure and reduces the risk of damage on the inner anatomical structures during insertion for a given insertion force. This greater contact area also means that larger electrode contacts can be used, so that in the case of applying electrical stimulation, that can occur at higher charges for given safe charge density limits. The improved geometry of the electrode also provides an ability to inject the current directionally where desired by proper arrangement of the electrode contacts; for example, towards the membranous labyrinth with an electrode contact on the inner concave surface, or towards the bony labyrinth with an electrode contact on the outer convex surface of the C-shaped electrode carrier.

There is always an uncertainty for the surgeon about exactly where the electrode opening 303 in a canal should be drilled because the exact location of the nerve endings 204 is not known. This uncertainty results to some extent in an unknown distance of the electrode contacts 307 to the nerve endings 204 after implantation. Sometimes this causes longer fitting sessions afterwards in order to adjust the optimal stimulation currents on each of the electrode contacts 307. This problem can be mitigated by using electrode contacts 307 with a greater longitudinal than radial extension which covers a larger longitudinal region for the provision of electrical stimuli. In particular, the most distal electrode contact 307 may be advantageously formed like this.

Although various exemplary embodiments of the invention have been disclosed, it should be apparent to those skilled in the art that various changes and modifications can be made which will achieve some of the advantages of the invention without departing from the true scope of the invention.

What is claimed is:

1. A vestibular electrode for implantation into a vestibular semi-circular canal having an inner membranous labyrinth separated from an outer bony labyrinth by surrounding perilymph fluid, the vestibular electrode comprising:

an intra-labyrinthine electrode carrier having radial outer ends and a C-shaped cross-section having an inner concave surface and an outer convex surface, the electrode carrier configured to fit through an electrode opening in an outer surface of the bony labyrinth into the perilymph fluid without breaking the membranous labyrinth so as to fit the inner concave surface of the electrode carrier adjacent to the membranous labyrinth and the outer convex surface adjacent to the bony labyrinth, the radial outer ends having, in part, a curved outer surface configured to engage against an inner surface of the bony labyrinth and configured to prevent overcompression of the membranous labyrinth during insertion; and one or more electrode contacts on a surface of the electrode carrier configured for electrical interaction with adjacent neural tissue.

2. The vestibular electrode according to claim 1, further comprising:

an extra-labyrinthine electrode lead having a distal end connected to the electrode carrier at the electrode opening at a connection angle configured to avoid over-insertion of the electrode carrier.

3. The vestibular electrode according to claim 2, wherein the electrode carrier further comprises a carrier angle adapted to change direction of the electrode carrier beyond the electrode opening to direct the electrode carrier between the bony labyrinth and the membranous labyrinth.

4. The vestibular electrode according to claim 1, wherein the electrode carrier is configured so that after implantation into a vestibular semi-circular canal, the electrode carrier has a proximal end near the electrode opening and terminal distal end away from the electrode opening, wherein the electrode carrier at the distal end is narrower than the electrode carrier at the proximal end.

5. The vestibular electrode according to claim 1, wherein the electrode carrier is configured so that after implantation into a vestibular semi-circular canal, the electrode carrier has a proximal end near the electrode opening and terminal distal end away from the electrode opening, wherein the electrode carrier at the proximal end and the distal end are narrower than the electrode carrier between the ends.

6. The vestibular electrode according to claim 1, wherein the one or more electrode contacts are on the outer convex surface of the electrode carrier to face the bony labyrinth.

7. The vestibular electrode according to claim 1, wherein the one or more electrode contacts are on the inner concave surface of the electrode carrier to face the membranous labyrinth.

8. The vestibular electrode according to claim 1, wherein there is at least one electrode contact on each of the outer convex surface and the inner concave surface of the electrode carrier.

9. The vestibular electrode according to claim 1, wherein the one or more electrode contacts include at least one stimulation contact for delivering an electrical stimulation signal to the adjacent neural tissue.

10. The vestibular electrode according to claim 1, wherein the one or more electrode contacts include at least one measurement contact for measuring electrical activity in the adjacent neural tissue.

11. A vestibular implant system having at least one vestibular electrode according to any of claims 1-10.

* * * * *